United States Patent [19]

Vagley

[11] Patent Number: 6,158,437

[45] Date of Patent: *Dec. 12, 2000

[54] METHOD OF PERFORMING A SURGICAL PROCEDURE AND ASSOCIATED SURGICAL INSTRUMENT SUPPORT TRAY

[76] Inventor: Richard T. Vagley, 830 15th St., Oakmont, Pa. 15139

[ * ] Notice: This patent issued on a continued prosecution application filed under 37 CFR 1.53(d), and is subject to the twenty year patent term provisions of 35 U.S.C. 154(a)(2).

[21] Appl. No.: 08/796,653

[22] Filed: Feb. 5, 1997

Related U.S. Application Data

[63] Continuation of application No. 08/417,498, Apr. 5, 1995, abandoned, which is a continuation of application No. 08/166,699, Dec. 14, 1993, abandoned.

[51] Int. Cl.$^7$ .................................................. B65D 85/62
[52] U.S. Cl. .......................... 128/898; 206/370; 206/570; 206/439; 206/561
[58] Field of Search ..................................... 206/369, 370, 206/438, 63, 557, 558, 562, 563, 564, 570; 433/77, 79; 128/898

[56] References Cited

U.S. PATENT DOCUMENTS

| D. 283,160 | 3/1986 | Steinman | D24/31 |
|---|---|---|---|
| 3,726,026 | 4/1973 | Borcherding | 35/62 |
| 4,046,254 | 9/1977 | Kramer | 206/370 |
| 4,153,160 | 5/1979 | Leigh | 206/370 |
| 4,266,669 | 5/1981 | Watson | 206/370 X |
| 4,596,329 | 6/1986 | Eldridge, Jr. | 206/370 |
| 4,793,483 | 12/1988 | Holmes | 206/438 X |
| 4,828,113 | 5/1989 | Friedland et al. | 206/369 X |
| 5,059,271 | 10/1991 | Taub | 156/306.3 |
| 5,174,453 | 12/1992 | Stoeffler | 206/570 |
| 5,289,919 | 3/1994 | Fischer | 206/63.5 |

*Primary Examiner*—Robert L. Nasser
*Attorney, Agent, or Firm*—David C. Jenkins; Arnold B. Silverman; Eckert Seamans Cherin & Mellott, LLC

[57] ABSTRACT

A method of performing a surgical procedure includes providing an instrument supporting tray having a plurality of surgical instruments positioned thereon adjacent to a plurality of instrument-identifying indicia disposed in predetermined relative positions. In performing the surgical procedure, the surgical instruments will be employed generally in the sequence in which they are positioned on the tray. The surgical instruments are identified by at least one of (a) graphics corresponding generally to the shape of the particular surgical instrument, (b) recesses conforming generally to the shape of the surgical instrument and (c) words and/or numbers providing identification thereof. In a preferred embodiment, the instrument-identifying indicia will be provided with different instruments in different sequences, depending upon the specific surgical procedure. In a further embodiment, the instrument-identifying indicia will be keyed both in terms of identity of instrument and sequence of presentation to the preference of the particular surgeon. The surgical instrument support of the present invention has a surgical instrument supporting surface for supporting a plurality of surgical instruments and instrument-identifying indicia disposed in predetermined relative position to establish a sequence which corresponds generally to the sequence in which the surgical instruments will be employed. The instrument-identifying indicia also serves to provide, by at least one of (a) graphics, (b) recesses and (c) words and/or numbers specific identification of the instrument.

26 Claims, 3 Drawing Sheets

METHOD OF PERFORMING A SURGICAL PROCEDURE AND ASSOCIATED SURGICAL INSTRUMENT SUPPORT TRAY

This is a continuation of U.S. patent application Ser. No. 08/417,498, filed Apr. 5, 1995, now abandoned, which is a continuation of U.S. patent application Ser. No. 08/166,699, filed Dec. 19, 1993 now abandoned.

BACKGROUND OF THE INVENTION

1. Field of the Invention

The present invention relates to a method of performing a surgical procedure and to an associated surgical instrument support tray and, more specifically, it relates to a system wherein instrument-identifying indicia are provided on a surgical instrument support tray in the general sequence in which the instruments will be employed in a particular surgical procedure.

2. Description of the Prior Art

The medical well-being of mankind has benefited tremendously in this century due to enhanced diagnostic and therapeutic equipment and procedures, improved pharmaceuticals and the enhanced skill of the surgeon.

Tremendous coordination is required in the surgical suite in order to successfully perform a surgical procedure. Not only are sterility and highly efficient coordination among the chief surgeon, assistants, nursing staff and anesthesiologists required to make a surgical procedure successful, but also efforts must be made to do no harm to the patient.

In a typical surgical procedure, a surgeon will employ a large number of hand-held surgical instruments in a specific sequence depending upon both the specific procedure being performed and the preference of the particular surgeon. As there are on the order of hundreds of different surgical instruments in general use, in addition to their being various sizes and other variations within these general categories, it becomes critical that the surgical assistants be able to deliver accurately the specific instrument called for by the surgeon in a rapid and highly reliable manner. Unfortunately, there are situations in the surgical environment wherein either experienced knowledgeable assistants make careless mistakes or assistants who are inadequately skilled are not able to identify by name the particular surgical instrument called for by a surgeon. Such errors can have a substantial detrimental impact upon the surgery.

U.S. Pat. No. 5,059,271 discloses the use of a sheet of silicone rubber with a non-slip surface with the material draped over the patient who is lying in a horizontal position. Surgical instruments are placed on this piece of material which is positioned in relatively close adjacency to the incision. It is stated that even though the surface may be inclined, the non-stick characteristics will resist undesired falling of the surgical instruments off of the sheet.

Despite the foregoing, there remains a need for improved handling of surgical instruments during surgery so as to enhance the likelihood that potentially life saving or life threatening surgical procedures can be performed with a higher degree of efficiency.

SUMMARY OF THE INVENTION

The above-described needs have been met by the present invention. The method of the present invention involves providing an instrument supporting tray having a plurality of surgical instruments positioned thereon. The tray has a plurality of instrument-identifying indicia disposed in a predetermined relative position corresponding to the general sequence in which they will be employed in the surgical procedure. The surgeon employs the surgical instruments generally in this sequence during performance of the surgical procedure.

The instrument-identifying indicia may be one or more of the following: (a) a graphic representation corresponding in general to the appearance of the instrument, (b) a recess for at least partially receiving the instrument corresponding generally to the shape of the instrument and (c) words and/or numbers identifying the name of the instrument.

In a most preferred embodiment of the invention, the sequence of representation of the instruments by the instrument-identifying indicia will be customized to not only the particular surgical procedure which will be performed, but also to the preference of the specific surgeon who will be performing the surgery.

The surgical tray of the present invention has an instrument-supporting surface and instrument-identifying indicia disposed in a predetermined sequence so as to facilitate presentation of the instruments in the sequence in which the surgeon will be performing the surgery as well as specific identification of the instrument.

The tray of the present invention is preferably flexible such that it can be stored in a rolled or folded condition. It is also preferably sterilizable. The instrument-identifying indicia may be presented as part of a separate element secured to the tray or be imprinted directly on a tray on one or both sides thereof.

It is an object of the present invention to provide a system for enhanced surgical efficiency through presentation on a tray of the surgical instruments to be used in a particular procedure in the general sequence in which they will be employed.

It is a further object of the present invention to provide instrument-identifying indicia on the tray so as to facilitate identification of the particular instrument for delivery of the same to the surgeon and identification of the place on the tray where the instrument is to be returned after use.

It is yet another object of the present invention to provide such a system which facilitates presenting additional equipment information reflecting preferences of the particular surgeon in a readily visible manner.

It is a further object of the present invention to provide, in one embodiment, such a system which is sterilizable and readily reusable.

It is another object of the invention to present additional information on the tray related to the specific surgical procedure.

These and other objects of the invention will be more fully understood from the following description of the invention in reference to the illustrations appended hereto.

DESCRIPTION OF THE PREFERRED EMBODIMENTS

As employed herein, the term "patient" means a member of the animal kingdom, including humans.

As employed herein, the term "surgical procedure" means a procedure performed on a patient by a physician, dentist, veterinarian or other legally authorized health care professional which procedure involves a plurality of hand-held instruments and is at least partially invasive.

As employed herein, "instrument-identifying indicia" means visually perceptible elements which will facilitate identification of a specific surgical instrument or its position on the tray.

Figure 1:
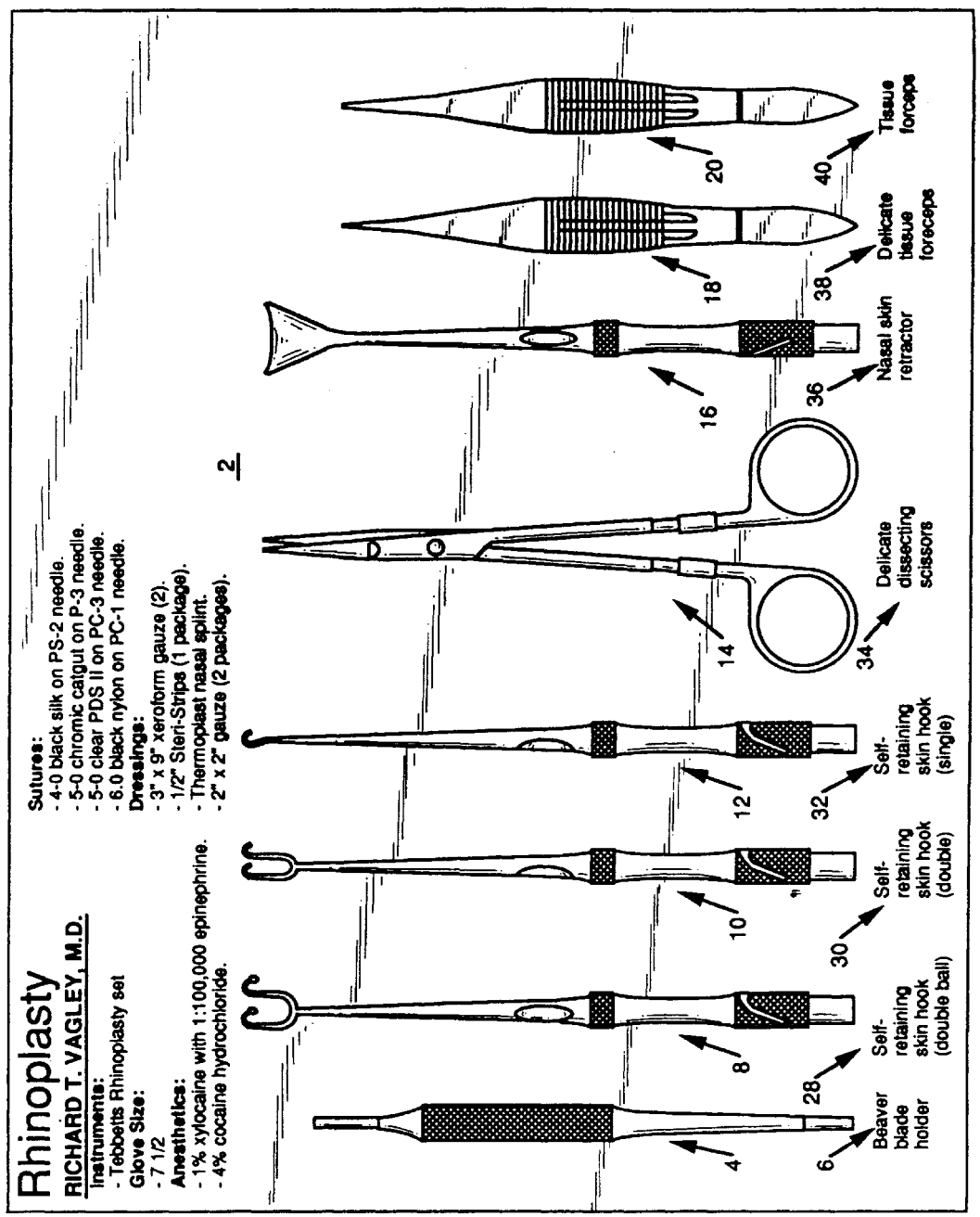
FIG. 1 is a top plan view of a form of tray of the present invention.

FIG. 1 shows a plan view of a tray of the present invention wherein a series of eight instruments will be employed in sequence going from left to right. As used herein the reference to "generally in the sequence" refers to the individual instruments being used by the surgeon in a specific surgical procedure starting from the left and going to the right and shall embrace instances where one or more of these instruments will, during the course of the procedure, be employed more than once. Such repeat usage of the particular instruments will not be deemed to depart from the expression "employed generally" in sequence.

In this embodiment, the tray 2 has instrument-identifying indicia in the form of both graphic planar representations and words. The first instrument 4 is identified by a graphic representation of the instrument and words 6 which identify it as a Beaver blade holder. Similarly, graphic presentation of instruments 8, 10, 12, 14, 16, 18 and 20 are presented along with corresponding word identifications 28, 30, 32, 34, 36, 38, 40.

These instruments have been selected as being the instruments desired to be used by the surgeon in performing a rhinoplasty surgical procedure. By providing the instruments on the tray 2 in this sequence and identifying the instrument both graphically and textually, the efficient presentation of the instruments to the surgeon by the surgical assistant is facilitated along with enhanced facility for returning the instrument to the proper location on the tray after use. As a result, when the procedure is beginning the surgical assistant will, when asked for a Beaver blade holder, provide to the surgeon the instrument positioned over graphic component 4 and adjacent to textual legend. Subsequently, when asked for a self-retaining skin hook (double ball) the instrument positioned over graphic element 8 will be provided. This procedure will be followed throughout the surgery. As the instruments are handed back to the surgical assistant, he or she, if not certain of the identity, can look at the graphic components and text for guidance and position the same over the desired location.

Figure 2:
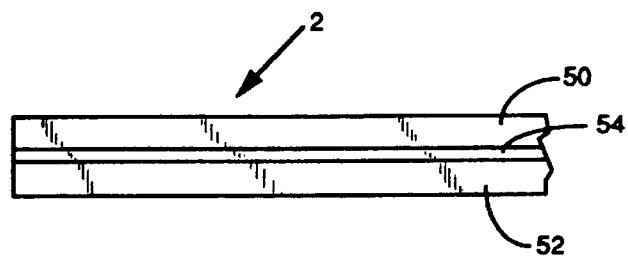
FIG. 2 is a partial end elevational view of a tray of the present invention showing the relative relationships of the materials.

In a preferred embodiment of the invention, the tray will be made of a flexible, sterilizble material which can be stored in a roll or folded without effecting meaningful damage thereto. Referring to FIG. 2, the tray may be made out of a silicone rubber material having an upper wall 50 and a lower wall 52. A pocket 54 is defined between walls 50 and 52 and may receive a plastic or paper element imprinted in the manner shown in FIG. 1. Assuming that the printed element received within pocket 54 faces upwardly, wall 50 should be transparent to facilitate ready reading of the words and viewing of the graphics. If desired, the separate element received within pocket 54 may be printed on both sides and both walls 50, 52 may be transparent thereby facilitating use of the instrument-identifying indicia in surgical procedures. In lieu of pocket 54, the separate element bearing the instrument identifying indicia may be secured to the outer surface of wall 50 or wall 52 by any suitable means such as adhesive or tape, or frictional retention. In the alternative, the separate element may be positioned over wall 50 or wall 52 and rest thereon without securement thereto. The separate element may be made of any suitable material, such as paper, paperboard, or plastic, for example.

As the reusable tray must be sterilizable, if the separate element received in pocket 54 cannot withstand such treatment, it will be removed with the tray 2 before sterilization.

An alternative approach would be to print the material shown in FIG. 1 on the outer surface of the tray or print the same and, if desired or required, provide a protective covering thereover subsequently. If desired, printing of a pattern, such as exemplified by FIG. 1, may be provided on both surfaces of the tray with different surgical procedures represented by each printed surface. The term "printing" as employed herein refers generically to any means of applying a different colored material to the tray so as to create readily visible graphic components or the words or numbers desired.

Referred once again to FIG. 1, there is shown in the upper left hand corner a further preferred feature of the present invention. While the general concept of the present invention involves positioning instruments sequentially in the order in which they will be employed for a particular surgical procedure adjacent to their respective instrument-identifying indicia, the invention also contemplates, if desired, providing further refinements which are keyed to the preferences of a particular surgeon. For example, the description herein-before has focused upon the example of rhinoplasty. The rhinoplasty tray 2 may be keyed to the instruments which Dr. Vagley prefers to employ in the procedure in his preferred sequence. It also may provide additional information regarding equipment preferences of Dr. Vagley in performing rhinoplasty such as the particular maker of the instruments, glove size, preferred anesthetics, sutures and dressings. The present invention facilitates providing such information as well.

In general, it will be preferred that the tray have a thickness which varies depending upon the material and construction employed. The tray may be of generally rectangular configuration and have outside dimensions no greater than the dimensions of the support surface on which it will be placed. If desired, the tray may be composed of a substantially rigid material.

It will be appreciated from the foregoing that the tray may be fully sterilizable in the portion where the printed indicia, such as paint, ink or different colored material, for example, are applied. The tray may also be fully sterilizable, subject to providing (a) an insert which might bear instrument-identifying indicia and be made of plastic or paper, for example, and positioned in pocket 54, or (b) a plastic or paper element, for example, bearing instrument-identifying indicia might be positioned on top of another portion of the tray, or (c) the tray may be fully disposable, such as by employing a paper or plastic item, for example, imprinted as shown in FIG. 1, for example, supported on a rigid support which need not be a portion of the tray, or (d) the tray may have an unsterilized element bearing the instrument-identifying indicia covered by a sterile transparent drape.

One of the advantages of employing the pocket is that the benefit of the instrument-identifying indicia is provided while the non-slip characteristics of the material out of which walls 50 and 52 are made are retained.

Figure 4:
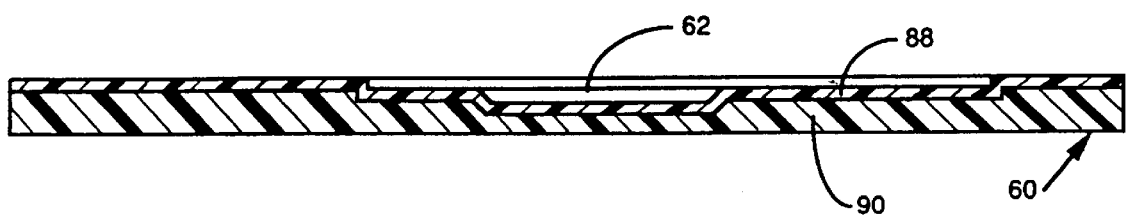
FIG. 4 is a cross-sectional illustration of the tray of FIG. 3 taken through 4—4 thereof.
Figure 3:
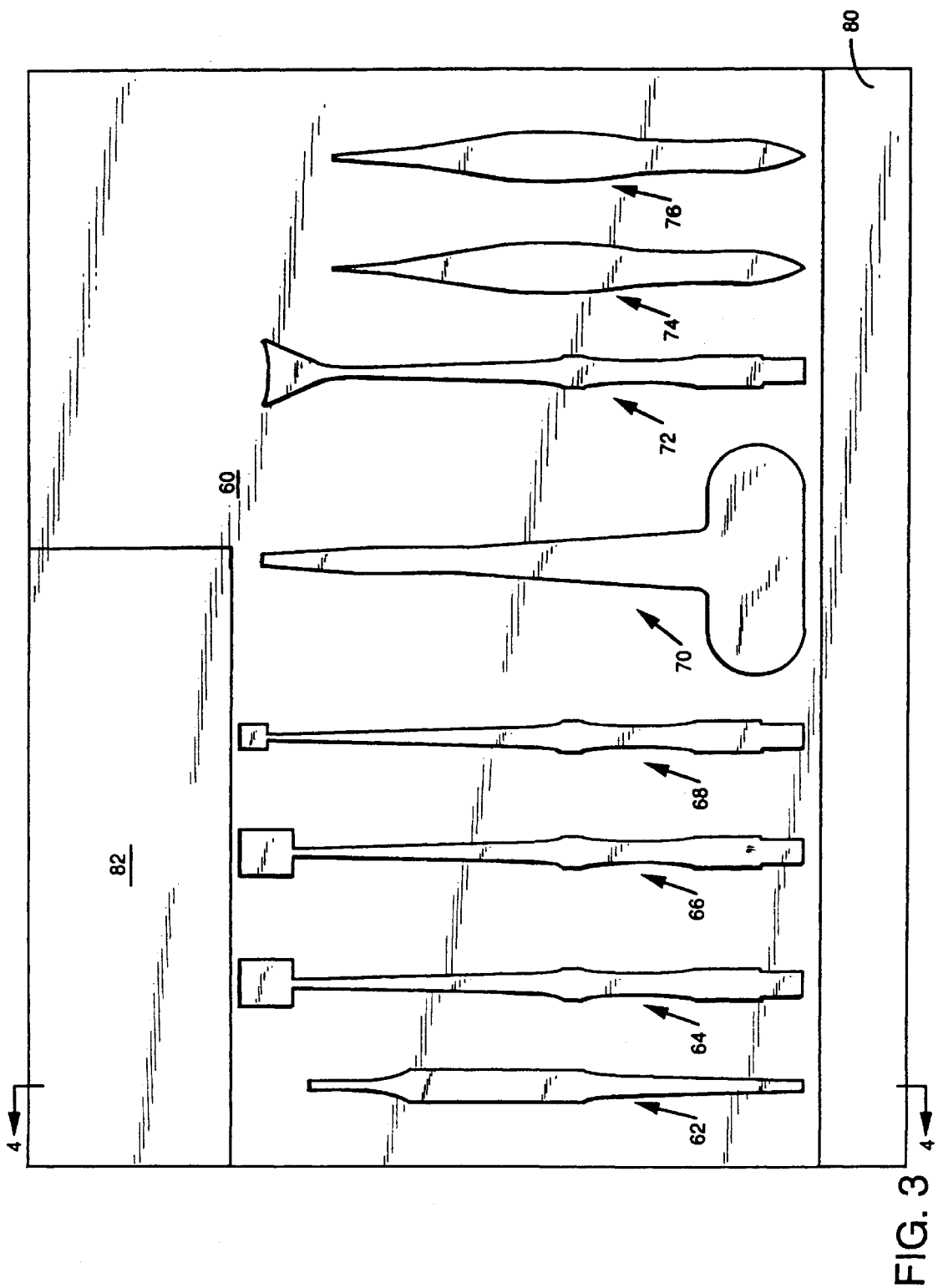
FIG. 3 is a top plan view of a modified form of tray of the present invention wherein recesses are provided for the instruments.

Referring to FIG. 3, a different embodiment of the present invention will be considered. In this embodiment, the tray 60 has a series of upwardly open recesses 62, 64, 66, 68, 70, 72, 74, 76 each being generally contoured so as to at least partially receive a specific surgical instrument. The recesses 62–76 (even numbers only) are so positioned as to provide the surgical instruments generally in the sequence in which they will be employed during the surgical procedure. In this embodiment, if desired, graphic representations of the specific instrument 62–76 (even numbers only) may be provided in addition to the recesses either within the recess or adjacent thereto. Also, textual and/or numeric identification (not shown) of the specific instruments are preferably provided within zone 80 with the words and/or numbers underlying the recess for the particular instrument. Information similar to that provided in the upper left corner of FIG. 1 may be provided in zone 82. As shown in FIG. 4, the recess 62 is upwardly open and may be formed within a molded element 88 which may form the upper portion of tray 60 which in turn may be received on any suitable underlying support member 90, such as a plastic or a metal underlying member to which it may be secured as by self-bonding or a suitable adhesive.

It will be appreciated, therefore, that the present invention not only provides for the surgical instruments to be supported on the tray in the sequence in which they will be employed during the surgical procedure, but also employs at least one of (a) graphic representation as in FIG. 1, (b) textual (or numeric) identification as in FIGS. 1 and 3 and (c) recesses as in FIGS. 3 and 4 to facilitate ready identification of the surgical instrument for purposes of delivery of the proper instrument to the surgeon in an efficient and promnpt manner and returning the instrument to the proper location on the tray after use. All of this is accomplished in an economical manner employing trays which may be rigid or flexible which are sterilizable, or disposable, or are covered by a sterile drape and can be employed economically either as reusable elements or sterile, disposable elements.

As a further enhancement, the trays may be imprinted so as to not only provide a desired sequence of use and identification of the respective surgical instruments, but also be further customized to cater to the preference of a specific surgeon during a specific procedure and in such case may also provide additional equipment preferences of the surgeon. All of this is directed toward enhanced efficiency in the surgical suite and more accurate and prompt delivery of the correct instrument to the surgeon and return of the same to the tray after use.

Whereas particular embodiments of the invention have been described herein, for purposes of illustration it will be evident to those skilled in the art that numerous variation of the details may be made without departing from the invention as to find in the appended claims.

I claim:

1. A method of performing a surgical procedure comprising
   providing a plurality of surgical instruments, each having an appearance,
   providing an instrument supporting tray having said plurality of surgical instruments positioned thereon,
   providing said tray with a plurality of instrument identifying indicia disposed in a sequence of predetermined relative positions with the identified surgical instruments positioned adjacent to said instrument identifying indicia respectively related thereto,
   performing a surgical procedure employing said surgical instruments generally in the sequence in which said instrument-identifying indicia are present, and
   employing a sterilizable flexible tray having a pocket for receipt of said instrument-identifying indicia and a transparent wall whereby said instrument-identifying indicia may be seen from the exterior of said tray.

2. The method of performing a surgical procedure of claim 1
   selecting and positioning said surgical instruments to correspond with the surgical procedure being performed.

3. The method of performing a surgical procedure of claim 2 including
   selecting and positioning said surgical instruments according to a specific surgeon's preference.

4. The method of performing a surgical procedure of claim 2 comprising
   employing as said instrument-identifying indicia at least one of (a) graphic representations corresponding generally to the appearance of said surgical instrument, (b) words, and (c) numbers.

5. The method of performing a surgical procedure of claim 4 including
   establishing said instrument-identifying indicia by printing on said tray.

6. The method of performing a surgical procedure of claim 2 including
   employing as said instrument-identifying indicia at least one of (a) recesses in said tray corresponding generally to the appearance of said surgical instrument, (b) words, and (c) numbers.

7. The method of performing a surgical procedure of claim 2 including
   employing as said tray a flexible tray which can be rolled or folded for storage.

8. The method of performing a surgical procedure of claim 2 including
   employing a sterilizable tray as said tray.

9. The method of performing a surgical procedure of claim 2 including
   employing a transparent sterile drape overlying said instrument-identifying indicia.

10. The method of performing a surgical procedure of claim 1 including
    employing at least some of said instruments more than once during said surgical procedure.

11. A method of performing a surgical procedure comprising:
    providing a plurality of surgical instruments, each having an appearance,
    providing an instrument supporting tray having said plurality of surgical instruments positioned thereon,
    providing said tray with a plurality of instrument identifying indicia disposed in a sequence of predetermined relative positions with the identified surgical instruments positioned adjacent to said instrument identifying indicia respectively related thereto, and
    performing a surgical procedure employing said surgical instruments generally in the sequence in which said instrument-identifying indicia are present;
    employing a sterilizable flexible tray, and securing an instrument-identifying indicia bearing element to said tray;

employing said tray having a pocket for receipt of said instrument-identifying indicia bearing element and a transparent wall whereby said instrument-identifying indicia may be seen from the exterior of said tray.

12. The method of performing a surgical procedure of claim 10 including positioning said tray on a generally rigid support surface during said surgical procedure.

13. The method of performing a surgical procedure of claim 1 comprising employing said process in a procedure performed on a human being by a surgeon.

14. The method of performing a surgical procedure of claim 13 including providing on said tray identification of said surgeon and said surgeon non-instrument surgical equipment preferences.

15. The method of performing a surgical procedure of claim 1 including the step of securing an instrument-identifying indicia bearing element to said tray.

16. A surgical instrument support tray comprising a surgical instrument supporting surface for supporting a plurality of surgical instruments, said surgical instruments being employable in a sequence in a surgical procedure, instrument-identifying indicia disposed in predetermined relative position generally corresponding to the sequence in which said surgical instruments will be employed, wherein each said instrument has an appearance; and said instrument-identifying indicia includes a visual depiction of said instruments established by a two dimensional graphics and recesses corresponding to the appearance of said instruments.

17. The surgical instrument support tray of claim 16 including said tray having said instrument-identifying indicia identifying the instruments and relative sequence of use for a particular surgeon in a specific surgical procedure.

18. The surgical instrument support tray of claim 16 including said tray having additional information regarding said surgeon's specific non-instrument equipment preferences.

19. The surgical instrument support tray of claim 16 including said tray being sterilizable.

20. The surgical instrument support tray of claim 19 including said tray being flexible so as to permit rolling or folding for storage without meaningful damage thereto.

21. The surgical instrument support tray of claim 20 including said instrument-identifying indicia being printed on said tray.

22. The surgical instrument support tray of claim 20 including said instrument-identifying indicia being printed on a separate element which is secured to said tray.

23. The surgical instrument support tray of claim 16 including a transparent sterile drape overlying the portion of said tray bearing said instrument-identifying indicia.

24. A surgical instrument support tray comprising:

a surgical instrument supporting surface for supporting a plurality of surgical instruments, said surgical instruments being employable in a sequence in a surgical procedure, instrument-identifying indicia disposed in predetermined relative position generally corresponding to the sequence in which said surgical instruments will be employed, said tray being sterilizable, said tray being flexible so as to permit rolling or folding for storage without meaningful damage thereto, said instrument-identifying indicia being printed on said tray, and said tray having a pocket within which said separate element is secured and an adjacent transparent tray wall to permit said instrument-identifying indicia to be viewed.

25. A surgical instrument support tray comprising:

a surgical instrument supporting surface for supporting a plurality of surgical instruments, said surgical instruments being employable in a sequence in a surgical procedure, instrument-identifying indicia disposed in predetermined relative position generally corresponding to the sequence in which said surgical instruments will be employed, said tray being sterilizable, said tray being flexible so as to permit rolling or folding for storage without meaningful damage thereto, said instrument-identifying indicia being printed on a portion of said tray, and said tray being printed with instrument-identifying indicia on a separate element which is positioned on another portion of said tray.

26. A surgical instrument support tray comprising:

a surgical instrument supporting surface for supporting a plurality of surgical instruments, said surgical instruments being employable in a sequence in a surgical procedure, and instrument-identifying indicia disposed in predetermined relative position generally corresponding to the sequence in which said surgical instruments will be employed, said tray being sterilizable, said tray being flexible so as to permit rolling or folding for storage without meaningful damage thereto, said instrument-identifying indicia being printed on a separate element which is secured to said tray, said separate element being printed with instrument-identifying information on both sides and said tray having two said transparent walls.

* * * * *